(12) United States Patent
Staal et al.

(10) Patent No.: US 8,465,637 B2
(45) Date of Patent: Jun. 18, 2013

(54) ION SENSOR FOR FLUID AND METHOD FOR ITS MANUFACTURE

(75) Inventors: Steven Selwyn Staal, Enschede (NL); Jan Floris, Enschede (NL); Albert Van Den Berg, Nijverdal (NL)

(73) Assignee: Medimate Holding B.V., Enschede (NL)

( * ) Notice: Subject to any disclaimer, the term of this patent is extended or adjusted under 35 U.S.C. 154(b) by 223 days.

(21) Appl. No.: 12/515,635

(22) PCT Filed: Nov. 21, 2006

(86) PCT No.: PCT/EP2006/011148
§ 371 (c)(1),
(2), (4) Date: May 20, 2009

(87) PCT Pub. No.: WO2008/061542
PCT Pub. Date: May 29, 2008

(65) Prior Publication Data
US 2010/0062082 A1 Mar. 11, 2010

(51) Int. Cl.
*G01N 27/453* (2006.01)
(52) U.S. Cl.
USPC .......................... 204/452; 204/451; 204/601
(58) Field of Classification Search
USPC .................. 204/450–455, 600–605
See application file for complete search history.

(56) References Cited

U.S. PATENT DOCUMENTS

| | | | |
|---|---|---|---|
| 3,506,554 A | 4/1970 | Broome | |
| 4,242,194 A | 12/1980 | Kaufman | |
| 4,956,062 A | 9/1990 | Ooi et al. | |
| 5,223,114 A | 6/1993 | Zare et al. | |
| 5,849,208 A | 12/1998 | Hayes et al. | |
| 5,882,496 A | 3/1999 | Northrup et al. | |
| 5,900,130 A * | 5/1999 | Benvegnu et al. | 204/453 |
| 5,955,028 A | 9/1999 | Chow | |
| 5,989,402 A | 11/1999 | Chow et al. | |

(Continued)

FOREIGN PATENT DOCUMENTS

| | | |
|---|---|---|
| CA | 2737892 | 9/2003 |
| EP | 215419 | 3/1987 |

(Continued)

OTHER PUBLICATIONS

R. W. Tjerkstra, et al., "Multi-Walled Microchannels: Free-Standing Porous Silicon Membranes for Use in [micro]TAS", Journal of Microelectromechanical Systems, vol. 9, No. 4, Dec. 2000, p. 495-501.*

(Continued)

*Primary Examiner* — J. Christopher Ball
(74) *Attorney, Agent, or Firm* — Stephen H. Eland; Dann, Dorfman, Herrell & Skillman (57) ABSTRACT

The invention provides a method for the measurement of a concentration of a charged species in a sample, the sample having a plurality of types of charged species and at least one insoluble component. The method comprises: providing the sample on a surface of a partly permeable layer (30); allowing components of the sample to pass through the partly permeable layer (30) into a channel (12); and separating the components into sections, such that each at least one of the sections substantially comprises a single type of the plurality of the types of charged species, and determining the charge concentration in the at least one of the sections.

20 Claims, 7 Drawing Sheets

PROCESS STEPS

U.S. PATENT DOCUMENTS

| | | | |
|---|---|---|---|
| 6,090,545 | A | 7/2000 | Wohlstadter et al. |
| 6,258,254 | B1 | 7/2001 | Miyamoto et al. |
| 6,399,025 | B1 | 6/2002 | Chow |
| 6,432,720 | B2 | 8/2002 | Chow |
| 6,444,474 | B1 | 9/2002 | Thomas et al. |
| 6,503,757 | B1 | 1/2003 | Chow |
| 7,217,352 | B2 | 5/2007 | Seino |
| 2002/0025576 | A1 | 2/2002 | Northrup et al. |
| 2003/0114785 | A1 | 6/2003 | Kikuchi et al. |
| 2003/0209314 | A1 | 11/2003 | Guo et al. |
| 2004/0021068 | A1 | 2/2004 | Staats |
| 2004/0086872 | A1 | 5/2004 | Childers et al. |
| 2004/0089546 | A1 | 5/2004 | Bahatt et al. |
| 2005/0268701 | A1 | 12/2005 | Hintsche et al. |
| 2005/0279635 | A1 | 12/2005 | Chow et al. |
| 2006/0204143 | A1 | 9/2006 | Shiota et al. |
| 2009/0302190 | A1 | 12/2009 | Trieu et al. |
| 2010/0062082 | A1 | 3/2010 | Staal et al. |

FOREIGN PATENT DOCUMENTS

| | | |
|---|---|---|
| EP | 0631133 | 4/2002 |
| EP | 952890 | 6/2005 |
| JP | 62069139 | 3/1987 |
| JP | 1158342 | 6/1989 |
| JP | 10311827 | 11/1998 |
| JP | 2000002677 | 1/2000 |
| JP | 2000227414 | 8/2000 |
| JP | 2000515630 | 11/2000 |
| JP | 2001258868 | 9/2001 |
| JP | 2003530566 | 10/2003 |
| JP | 2005331411 | 2/2005 |
| JP | 2006047321 | 2/2006 |
| KR | 20000066685 | 11/2000 |
| WO | 96/33405 | 10/1996 |
| WO | 98/05424 | 2/1998 |
| WO | 01/77641 | 10/2001 |
| WO | 2005/003724 | 1/2005 |
| WO | 2005/094286 | 10/2005 |

OTHER PUBLICATIONS

Vrouwe et al., "Direct Measurement of Lithium in Whole Blood Using Microchip Capillary Electrophoresis With Integrated Conductivity Detection", Electrophoresis, vol. 25, 2004, pp. 1660-1667 (XP002447049).

Vrouwe et al., "Microchip Analysis of Lithium in Blood Using Moving Boundary Electrophoresis and Zone Electrophoresis", Electrophoresis, vol. 26, 2005, pp. 3032-3042 (XP002447050).

Japanese Official Action issued in Application No. 2009/537484 on May 12, 2011.

Examination Report dated Jul. 12, 2010 issued in EP Appl. No. 06818703.8.

International Search Report and Written Opinion of the International Searching Authority dated Aug. 30, 2007 issued in PCT/EP06/11148.

Vrouwe et al, Microchip Capillary Electrophoresis for Point-Of-Care Analysis of Lithium, Clincal Chemistry, 53:1, 2007, pp. 117-123.

Extended European Search Report issued in European Patent Application No. 12175953.4 on Jan. 14, 2013.

* cited by examiner

TOP VIEW a)

b)

c)

d)

SIDE VIEW e)

Fig. 1

EXPLODED VIEW

Fig. 2

PROCESS STEPS

ION SENSOR FOR FLUID AND METHOD FOR ITS MANUFACTURE

FIELD OF THE INVENTION

The invention relates to sensors of charged species in biological, chemical, industrial or environmental samples. In particular, the invention relates to a method and a sensor for measuring charged species concentrations, in particular ion concentrations, for example lithium ion concentrations, in samples, such as blood. The invention also relates to a method for the production of such a sensor.

BACKGROUND AND RELATED ART

Inorganic ions are an essential requirement for life and are found in large amounts in drinking water, blood and every cell of an organism as well as in the environment. For example, the concentration of many ions i.e. sodium, potassium, magnesium, and calcium inside and outside of cells is essential for any living organism. Consequently, the ion concentration in the blood and blood cells of animals and human beings also is of high importance for a large variety of body functions.

Normally lithium is a trace element present in the blood plasma, but it is used as a drug to treat bipolar mood disorder. It is estimated that worldwide over one million people take lithium on a daily basis. A disadvantage in the use of lithium is the very low therapeutic index, i.e., the ratio between the toxic concentration and the therapeutic concentration. Most patients respond well to a blood plasma concentration of 0.4-1.2 mmol/L lithium while toxic effects can occur at a lithium concentration of above 1.6 mmol/L. A prolonged high blood lithium level can even result in permanent damage to the nervous system and even death. Monitoring of the lithium concentration during treatment is therefore essential, with regular checks every couple of months to keep the lithium level at desired level.

To avoid extensive operator handling, ion-selective electrodes (ISEs) are routinely used for measurements of blood parameters in an automated fashion. These ISEs are fast and offer a large dynamic range; however, their response is logarithmic and the required high selectivity for lithium can be a problem. Additionally, in case of lithium intoxication a fast procedure for blood analysis is required. Currently, a venous blood sample must be withdrawn from the patient by specially trained personnel and transported to the central laboratory and the blood cells need to be removed before the measurement is made. This procedure can take up to 45 minutes. To minimize sample throughput time and enable measurements on location, miniaturized devices employing ion-sensitive field-effect transistors are available to determine the concentration of potassium and sodium in whole blood even as a hand-held analyzer. However, such analyzers are not used for lithium determination, because of the high background concentration of other charged species, in particular sodium ions, compared to to the much smaller concentration of lithium ions.

The direct measurement of lithium in whole blood and the determination of inorganic cations in blood plasma have been described and demonstrated by E. Vrouwe et al. in *Electrophoresis* 2004, 25, 1660-1667 and in *Electrophoresis* 2005, 26, 3032-3042. Using microchip capillary electrophoresis (CE) with defined sample loading and applying the principles of column coupling, alkali metals were determined in a drop of whole blood. Blood collected from a finger stick was transferred onto the chip without extraction or removal of components. The lithium concentration can be determined in the blood plasma from a patient on lithium therapy without sample pre-treatment. Using a microchip with conductivity detection, a detection limit of 0.1 mmol/L has been obtained for lithium in a 140 mmol/L sodium matrix.

In these disclosures, the components of the blood sample are separated electrophoretically inside a micro-channel. A double T injection geometry is used to select the ion components of interest and to guide them to detection electrodes.

In these systems, the sampling loading has to be well defined in order to ensure the correct separation of blood plasma components in the double T geometry. In addition, the double T geometry is complicated to apply and not well suited for easy to use applications.

SUMMARY OF THE INVENTION

The invention provides a method for the measurement of a concentration of a charged species in a sample, the sample having a plurality of types of charged species and at least one insoluble component, the method comprising: providing the sample on a surface of a partly permeable layer; allowing components of the sample to pass through the partly permeable layer into a channel; and separating the components into sections, such that each at least one of the sections substantially comprises a single type of the plurality of the types of charged species, and determining the charge concentration in the at least one of the sections.

Thus, the invention provides a method for dividing a sample, in particular a biological sample such as blood plasma into sections, each section comprising substantially one or a one group of charged species and subsequently determining the concentration of charged species in this section.

The invention also provides an apparatus for the measurement of a concentration of a charged species in a sample, the sample comprising a plurality of types of charged species and at least one insoluble component, the apparatus comprising at least one channel with at least one opening, a partly permeable layer covering the at least one opening, at least two electrophoresis electrodes arranged along the at least one channel on each side of the opening, and at least one sensor for measuring at least one type of charged species in the at least one channel.

The method and the apparatus are particularly useful for the measurement of ion concentrations of biological samples, for example blood plasma. The ions measured include but are not limited to sodium, potassium magnesium, calcium and the like. In one application of the invention, the sample may also contain lithium. In this case, the preferred ion to be measured is lithium but may be any other ion present in the sample. The invention is equally applicable to other charged species such as lipids, DNA or other polyelectrolytes or electric charge carrying polymers.

The concentration of a first one of the plurality of type of charged species may be determined relative to a second one of the plurality of the types of charged species. The first type of charged species may be lithium ions and the second type of charged species may be sodium ions; thus the ratio between lithium and sodium ions in the sample can be determined.

The at least one channel may have a single opening covered by a partially permeable layer. Using the single opening for sample application, electro-osmotic pressure or hydrodynamic pressure and any hydrodynamic flow inside the channel can be advantageously avoided. In that way, diffusion is the main or only transport mechanism.

In one embodiment, the at least one channel may have two openings in the otherwise sealed channel system. Using hydrodynamic pressure sample injection is realized by convective flow form one opening towards the other. In this specific case one opening is covered with the sample while the other opening is not.

The partially permeable layer may be a membrane separating the sample from the at least one channel. The membrane may be permeable to ions or other charged species while the membrane may be impermeable to larger components. In particular, the membrane may be impermeable to the insoluble component. The membrane may also be a gas-permeable membrane that is impermeable to liquids. The partially permeable layer may be a separate layer placed on top or below the at least one opening of the first cover layer.

A membrane holder may be used on the first cover layer for placing the membrane on the first cover layer. The membrane holder may be attached, i.e. glued the first cover layer or formed directly in the first cover layer.

The permeable layer may also be a region of the first cover layer that is made partially permeable. The permeable layer may comprise at least one region with a hydrophilic surface. Additionally, the permeable layer or the first cover layer may comprise at least one region with a hydrophobic surface.

The permeable layer may also consist of one or more holes in the channel. The sample may thus come into direct contact with a solution inside the channel.

The sample also comprises at least one insoluble component, i.e. in the case of a biological sample such as blood, red blood cells, white blood cells, platelets and the like that are usually present in the blood. Thus the present invention advantageously allows for the determination of an ion concentration in whole blood without prior purification or treatment thus avoiding any laboratory pre-treatment of the sample. The invention is therefore particularly useful for the application in patient operated system that do not require a specially trained physician or medical care taker.

The at least one sensor comprises one or more pairs of conductivity electrodes for determining the charge concentration in the at least one of the sections substantially comprising the single type of the plurality of the types of charged species. For example, a first pair of conductivity electrodes may be arranged in or nearby the channel at some distance from the at least one opening for measuring the concentration of charged species of a first polarity. A second pair of conductivity electrodes may be arranged at the opposite end of the channel for determining the concentration of a second charged species of opposite polarity to the first polarity.

The invention also provides a method for the manufacture of an apparatus for measuring the concentration of charged species in a sample, the method comprising providing a substrate, forming a channel into the substrate, placing a first cover layer on the substrate, such that the first cover layer covers the channel, whereby the first cover layer comprises at least one opening providing access to the channel, and placing a partly permeable layer on the at least one opening.

Using this method for the production of the apparatus, the partly permeable layer may be placed on the at least one opening prior to, after or simultaneously with placing the first cover layer on the substrate.

Prior to use of the apparatus, the at least one channel may be filled with an electrolyte. In one embodiment the filling of the channel comprises evacuating air and sucking electrolyte into the channel. The electrolyte may be filled into the at least one channel prior to covering the channel with a second cover layer.

DESCRIPTION OF THE DRAWINGS

The invention may be better understood with respect to the figures and the detailed description of preferred embodiments, which is illustrative only and not limiting to the invention and wherein.

In the figures same reference numerals describe the same or similar objects.

DETAILED DESCRIPTION OF THE INVENTION

FIGS. 1a to 1d show the components of an apparatus according to the invention in a top view.

Figure 1:
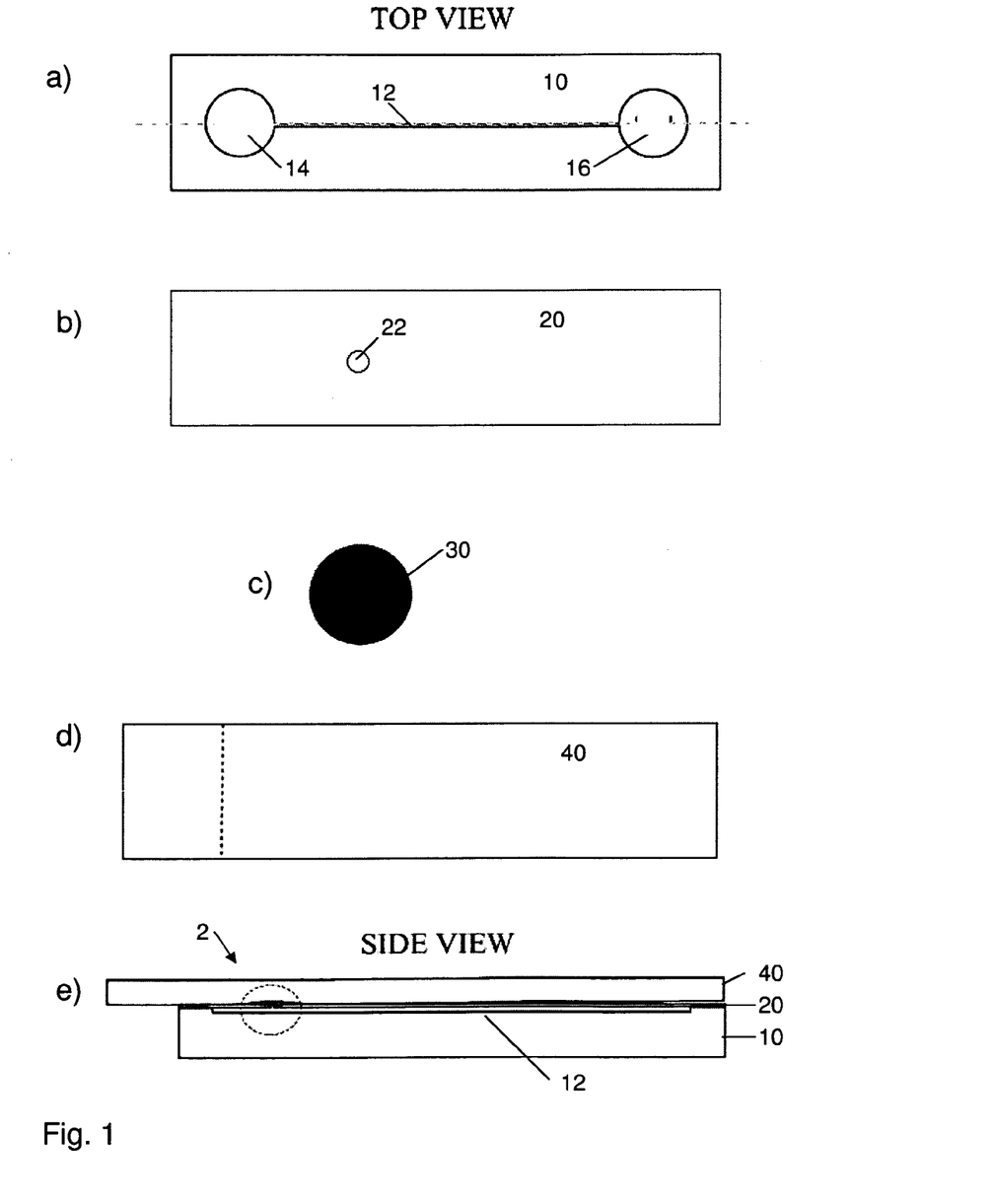
FIGS. 1a to 1d show main components of an apparatus according to the invention in a top view and FIG. 1e shows a side view of the components of FIGS. 1a to 1d assembled to an apparatus according to the invention.

The apparatus comprises a substrate 10 into which a channel 12 is formed, as shown in FIG. 1a. The substrate 10 may be made from glass or plastics material. Any other material allowing for the fabrication of channels 12 may be used. In case of glass as the substrate material, the channel 12 is etched into the substrate 10 between a first reservoir 14 and a second reservoir 16 and the side walls of the channel 12 are coated with a polymer. The channel 12 may be of sub-centimeter dimensions, in particular the channel 12 may be less than 1 cm in width and less than 100 µm in depth. The first reservoir 14 and the second reservoir 16 may be considerably larger in size than the width of the channel 12 (e.g. 100 µm to 1 cm), but may have substantially the same depth. The channel 12 and the first reservoir 14 and the second reservoir 16 may be filled with an electrolyte prior to use. This can be done, for example, by evacuating the channel 12, the first reservoir 14 and the second reservoir 16 and then allowing the electrolyte to be sucked into the channel 12 and the first reservoir 14 and the second reservoir 16. The first reservoir 14 and the second reservoir 16 can for example serve for equilibrating pressure differences to ensure that the channel 12 is always filled with the electrolyte.

The channel 12 may also be made of a plurality of nanochannels having a width of between 1 and 500 nm. The small size of the nanochannels suppresses hydrodynamic and electro-osmotic pressure within the channel 12.

The apparatus further comprises a first layer 20 shown in FIG. 1*b* as a cover layer for covering in use the substrate 10 and for closing the channel 12 to prevent in use any fluid like the electrolyte and the sample inside the channel 12 from evaporation or leaking out of the channel 12. The first layer 20 may be made for example, from glass, a polypropylene film or hydrophobic membrane, such as those supplied by the Pall Corporation under the designation Supor Membrane Disk Fillers (hydrophilic polyether sulfone) or Millipore Durapor (polyvinylidene—PVDE) and may have a thickness of less than 1 mm, in particular less than 1 μm. The first layer 20 is non permeable. The first layer 20 provides a first opening 22 to be arranged on top of the channel 12 in order to provide access for the sample to the channel 12.

The access opening 22 may have the form of a circle but any form suitable for inserting liquid into the channel may be used.

In addition, according to the invention a membrane 30 is provided, shown in FIG. 3*c*. In the example shown, the membrane 30 is in use arranged on top or below of the opening 22 of the first layer 20. The membrane 30 may be made of a permeable hydrophilic and/or biocompatible polymer of 1 to 100 μm thickness that is semipermeable, for example, nitrocellulose. It is possible that the membrane 30 be placed on the channel 12 prior to the first layer 20. Thus the membrane 30 may also be arranged between the first layer 20 and the substrate 10. The membrane 30 may also be integrated into the first layer 20. In any case, the membrane 30 is hydrophilic and can be made, for example, from nitrocellulose.

The size and the properties of the membrane 30 may be adapted to allow for diffusion of species or transfer of a specified volume of a sample from the sample side to the inside of the channel 12 in order to enable comparable measurements.

According to one aspect of the invention, the membrane 30 is permeable to blood plasma and its components in the sample but filters out larger insoluble components such as cell material in the sample or the like. In this way, cell material like red blood cells, white blood cells, platelets or the like are filtered out and only blood plasma enters the channel 12 for further examination. Other components may also be filtered out.

According to another aspect of the invention, the membrane 30 is permeable to charged species inside the blood plasma and the membrane 30 covered first opening 22 is the only opening to the channel. It may also be the only opening enabling convective flow into the channel 12. In that way convective flow is suppressed and at least the blood plasma and all kinds of cell material are prevented from entering the channel while only the charged species, in particular the ions diffuse into the channel 12 for further examination.

In a further embodiment of the invention, the membrane 30 and the first layer 20 might be made in a single step in which the first layer 20 is a polymer film which is made to act locally as a membrane or the first layer 20 is a polymer film in which the full polymer film is a membrane in which the hydrophobicity is altered. In the latter case, the hydrophobicity of the film is changed such that the film is hydrophilic at the position at which the sample is to be injected.

More than one access opening 22 may be made in the first layer 20. This is useful, for example, for allowing the sample to enter into the channel 12 at multiple entry points. This allows for multiple measurements to be made and averages to be taken. One further advantage of more than one access opening 22 is to allow convective flow from one opening towards another opening and thus providing an alternative transport mechanism through the opening 22 into the channel 12.

The membrane 30 can also be provided with microneedles on its surface to puncture the skin to obtain the sample more easily. Furthermore the membrane 30 could itself be punctured to realize, alter or improve its porosity.

A second polymer film 40 shown in FIG. 1*d* is provided for covering the first layer 20 and the semipermeable membrane 30 in order to protect the first layer 20 and the semipermeable membrane 30 from contamination, to keep them sterile and/or clean prior to use and to prevent leakage of fluid from the channel. Should the semipermeable membrane 30 have microneedles, these microneedles are also protected by the second polymer film 40. The second polymer film 40 is made of, for example, polypropylene. The second polymer film 40 may be removed immediately prior to use and a blood sample, i.e. a droplet of whole blood may in use be placed on top of the semipermeable membrane 30. The second polymer film 40 may have a loose end so that it can be easily gripped to be removed prior to use of the apparatus 2.

FIG. 1*e* shows a side view of the components of FIGS. 1*a* to 1*d* assembled as an apparatus 2 according to the invention. The first layer 20 is placed in top of the substrate 10 thus covering the top side of the channel 12. The first layer 20 has an opening 22 arranged on top of the channel 12. The opening 22 is covered by the membrane 30. In the case shown in FIG. 1*d* the apparatus 2 is covered by the second polymer layer 40 covering the whole or part of surface of the apparatus 2 and thus protecting the apparatus 2 from damage, dust, evaporation, etc.

The first layer 20 may also include hydrophobic membranes permeable to gas. The function of the gas permeable hydrophobic membrane is to prevent over pressure which might build up in the channel 12 as will be explained later. The gas permeable hydrophobic membrane might be applied separately but also embedded in the first layer 20.

Figure 2:
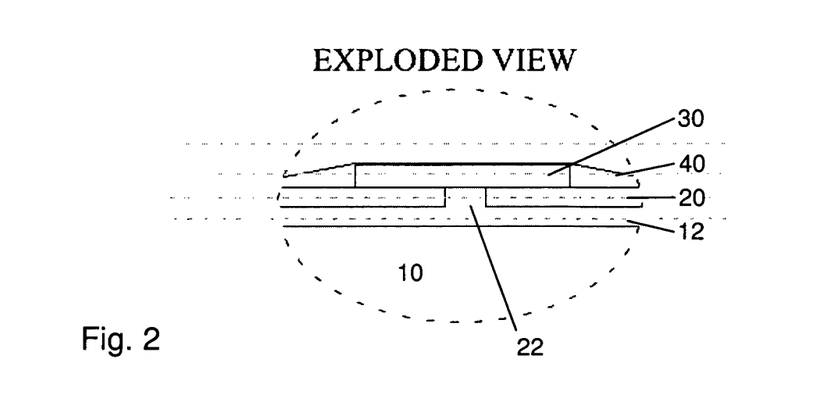
FIG. 2 shows a section of FIG. 1e in greater detail

FIG. 2 shows an exploded view of the area marked by a circle in FIG. 1*e* in greater detail. The membrane 30 is placed on top of the opening 22 in the first layer 20. The first layer 20 covers the channel 12 in the substrate 10 leaving an access to the channel 12 via opening 22. The opening 22 is covered by the membrane 30, thus, in use, only components that can diffuse or pass otherwise through the membrane 30 can access the channel 12. For protection and for preventing unwanted access to or contamination of the membrane 30, the membrane 30 is covered by a second polymer film 40. The membrane may be glued or otherwise fixed on, under or in the first layer 20. It would be possible to mount the membrane 30 in a holder and insert this holder in the opening 22 of the first layer 20. An example of a holder is described below with respect to FIG. 7.

The channel 12 may be coated with polymers in order to suppress electro osmosis flow as is known in the art.

FIGS. 3*a* to 3*f* show the main steps for providing the sample to be measured to the channel 12 in the enlarged and detailed view of FIG. 2.

FIG. 3*a* illustrates a detailed view of the apparatus of FIG. 2, whereby the channel 12, the opening 22 and the membrane 30 are filled with a background solution (shown as grey areas in the FIG.). For the detection of lithium, the background solution can be a background electrolyte (BGE) solution containing for example 50 mmol/L 2-(N-morpholino)ethanesulfonic acid and 50 mmol/L histidine at pH 6.1. Glucose may be added, for example about 200 mmol/L for adjusting the osmotic strength of the background solution. Other background solutions may be used depending on the charged species, i.e. the ion to be measured. The second polymer film 40 protects the apparatus 2 and the solution and prevents the solution from being contaminated prior to use. FIG. 3*a* illustrates the form in which the apparatus 2 may be shipped to a user.

FIG. 3*b* shows the removal of the second polymer film 40 prior to use of the apparatus 2. The second polymer film 40 serves as a protecting layer for protecting the membrane 30 and the first polymer layer 20 during shipping and storage of the apparatus 2. As shown in FIG. 3*b*, the second polymer film 40 is removed from the apparatus 2 in order to provide access for the sample to the membrane 30. The second polymer film 40 is provided with a quick release mechanism, such as a pull-tab, to allow easy removal of at least part of the second polymer film 40.

Prior to placing the sample on the membrane illustrated in FIG. 3*c*, one or more apparatus parameters, such as the conductivity of the electrolyte or temperature may be measured, for calibration or as a system check. A conductivity measurement of the pure electrolyte may also be performed as a system check, i.e. to check that electrolyte is present in the channels and that the measurement system is working correctly. It is advisable to flush the channel 12 electrokinetically prior to carrying out the measurement. This is to get rid of the first diffused parts of the sample in the channel 12. The conductivity measurement might be used for temperature measurements. The conductivity measurement might also be used as an internal check of the condition of the apparatus 2. The later might be realized with another temperature measurement method implemented somewhere in or around apparatus 2.

Heating elements may be placed inside or around the channel 12 or around the apparatus to alter the temperature of the liquid in the channel 12. The change of conductivity as a function of temperature may be used for control or calibration.

In FIG. 3*c* a sample 50, i.e. an untreated whole blood sample, is placed on the upper surface of the membrane 30. The membrane 30 is hydrophilic and permeable. Thus the sample 50 will be absorbed and pass through the membrane 30 as shown in FIG. 3*d*, whereby cell material such as red blood cells, white blood cells, etc are filtered out. This is done as the cell material might break down inside the channel 12 and alter the concentration inside the channel 12. The size of the pores of the membrane 30 might also be adjusted to filter out, for example, lipids or other larger components so that only electrolytes pass into the channel 12. Diffusing through the membrane 30, the filtered sample 50 will come in contact with the first layer 20 and enter into the opening 22.

As illustrated in FIGS. 3*d* and 3*e*, the filtered sample 50 diffuses through the opening 22 into channel 12 of the substrate 10. The amount of the filtered sample 50 reaching the channel 12 is determined by the size of the opening 22, the properties of the membrane 30, the properties of the sample 50 as well as the electrolyte present in channel 12.

FIG. 3*f* illustrates how a portion of the filtered sample 50 that diffused into the channel is electrophoretically separated in the channel 12 when an electrical field is applied along the channel 12. The electrical field will separate all of the charged species in the filtered sample and move the charged species towards the reservoirs 14 and 16 at the end of the channel 12.

Electrodes for providing an electrical field along the channel 12 may be imbedded or inserted in the first reservoir 14 and the second reservoir 16. It is also possible that a plurality of electrodes are placed along the channel 12 to create extra strong fields at those locations where the separation of the ions is necessary, by switching the electric field from one area to another. It was explained above that gas permeable hydrophobic membranes are used in the apparatus to prevent overpressure off gas. This overpressure may occur at the electrodes because of electrolysis.

The measurement may be performed repeatedly.

Figure 4:
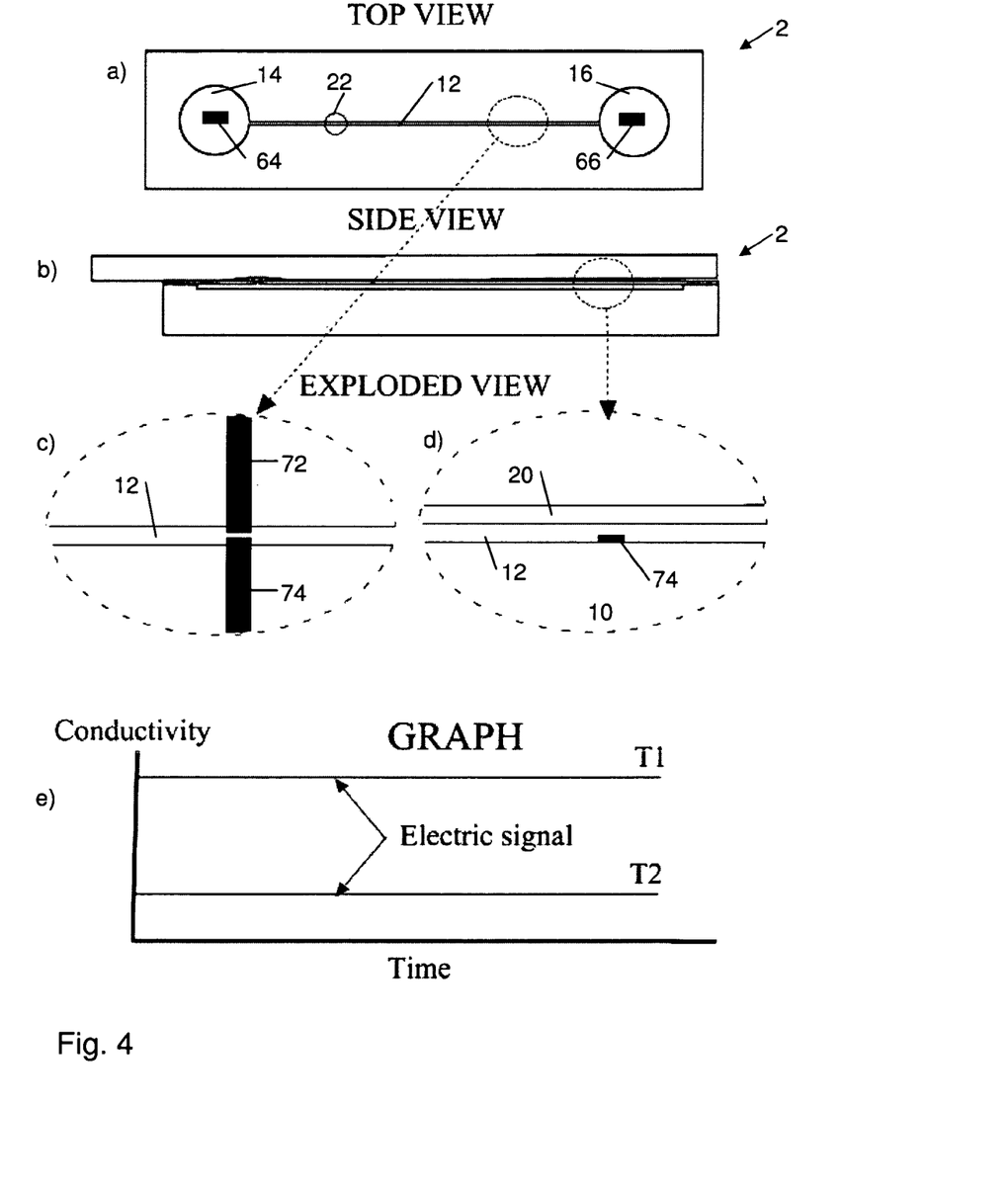
FIGS. 4a and 4b show an example of an apparatus according to the invention in top view and in side view, respectively.
FIG. 4c and FIG. 4d show electrode configurations for conductivity detection, both, contactless (FIG. 4c) and in contact conductivity detection (FIG. 4c and FIG. 4d) are possible realizations.
FIG. 4e shows two possible background measurement signals at for example two different measurement temperatures.

FIGS. 4*a* and 4*b* show an example of an apparatus 2 according to the invention in top view and in side view, respectively, wherein the first reservoir 14 comprises a first electrophoresis electrode 64 and the second reservoir 16 comprises a second electrophoresis electrode 66. By applying an electrical voltage to the electrophoresis electrodes 64, 66, charged particles inside the channel 12 may be separated or moved along the channel 12. The electrophoresis electrodes 64, 66 may be made of any conducting material. Examples of electrodes used include, but are not limited to, titanium electrodes with a chrome layer or silver/silver chloride electrodes The electrophoresis electrodes 64, 66 can be integrated in the substrate 10 or may be otherwise mounted into the reservoirs 14 and 16 or any other place in channel 12.

In an alternative embodiment, the electrophoresis electrodes 64, 66 and/or the conductivity electrodes 72, 74 may be mounted to a measurement device on which the apparatus 2 can be mounted for measurement.

The electrodes 72, 74 are not limited to a solely two-way electrode arrangement but can exist of multiple electrode arrangement.

A voltage may be applied to the electrophoresis electrodes 64, 66 by a power supply or any means known in the art.

FIG. 4*c* shows an exploded top view of the area marked by a circle in FIG. 4*a* and FIG. 4*d* shows an exploded side view of the same area in a side view, as also marked by a circle in FIG. 4*b*. In this area two conductivity electrodes 72 and 74 are provided in close proximity to or inside the channel 12 for measuring the conductivity of the fluid across the channel 12 at the position of the conductivity electrodes 72, 74. The conductivity electrodes 72 and 74 may be integrated in the substrate 10 and at least partially extend into the channel 12. As shown in FIG. 4*d*, the conductivity electrodes 72, 74 may be arranged on the bottom of the channel 12 but any other position at the channel 12 is possible. The conductivity electrodes 72, 74 may be connected to conductivity measurement known in the art.

In one embodiment of the invention, two pairs of conductivity electrodes 72 and 74 are used. One of the pairs of conductivity electrodes measures positive ions and the other one of the pairs of conductivity electrodes measures negative ions in the channel 12. The two pairs of conductivity electrodes 72 and 74 are placed on either side of the opening 22 through which the sample enters into the channel 12.

Placement of the conductivity electrodes 72 and 74 as well as the electrophoresis electrodes 64, 66 may be carried out during or after the manufacture of the apparatus 2. For example, the conductivity electrodes 72 and 74 and the electrophoresis electrodes 64, 66 may be pushed through the surface of the polymer cover 20 or the substrate 10 into the channel 12; thus costly implementation of the conductivity electrodes 72 and 74 and the electrophoresis electrodes 64, 66 in the chip can be avoided.

The conductivity in the channel 12 between conductivity electrodes 72 and 74 can be monitored over time. In case no charged component or an equal distribution of charged particles is present inside the channel, for example the BGE solution, a constant or relatively slowly varying conductivity will be measured and monitored as illustrated in FIG. 4*e*.

Figure 3:
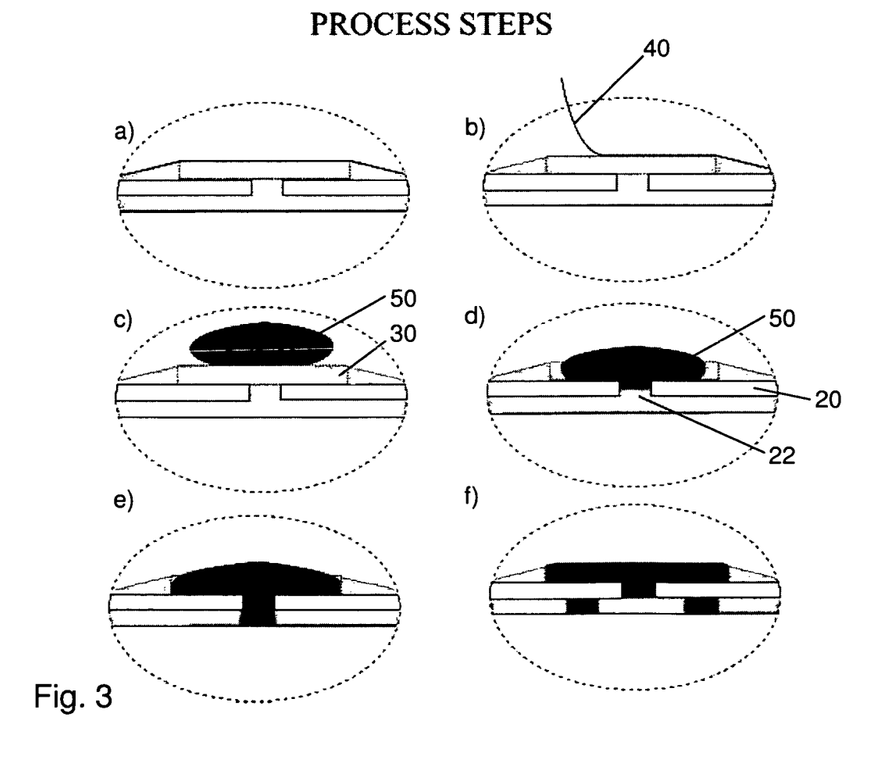
FIGS. 3a to 3f show main steps for providing a sample to be measured to the micro channel in the enlarged and detailed view of FIG. 2.

In case of the insertion of charged species, such as ions or the like, into the channel 12 using the method described with respect to FIG. 3, the charged species are moved along the channel 12 by an electric field applied between the electrophoresis electrodes 64 and 66. The charged species will be separated electrophoretically while travelling along the channel 12. For example, Na-ions of a blood sample 50 will move faster than Li-ion that may also be present in the blood sample 50. Thus, two peaks will be measured consecutively by the conductivity electrodes 72 and 74. A first peak represents the faster moving Na-ions passing the conductivity electrodes 72 and 74 and a second peak represents the slower moving Li-ions passing the conductivity electrodes 72 and 74. It is obvious to the person skilled in the art that more than two types of ions can be measured and that any charged component that may be separated by electrophoresis means can be monitored in that way.

The invention may be applied to measure absolute ion concentrations or for the measurement of relative ion concentrations, i.e. for the measurement of Na/Li-concentration ratios.

Further measurement electrodes or other types of sensors, i.e. optical sensors such as fluorescence sensors as known in the art may be added to measure the concentration or presence of further species in the sample within the same measurement. Capacitative sensors can also be used.

Prior to the measurement of the concentration of the charged species, such as ions, it is useful to measure the conductivity of the electrolyte in combination with the temperature of the apparatus to ensure that apparatus is performing correctly.

Figure 5:
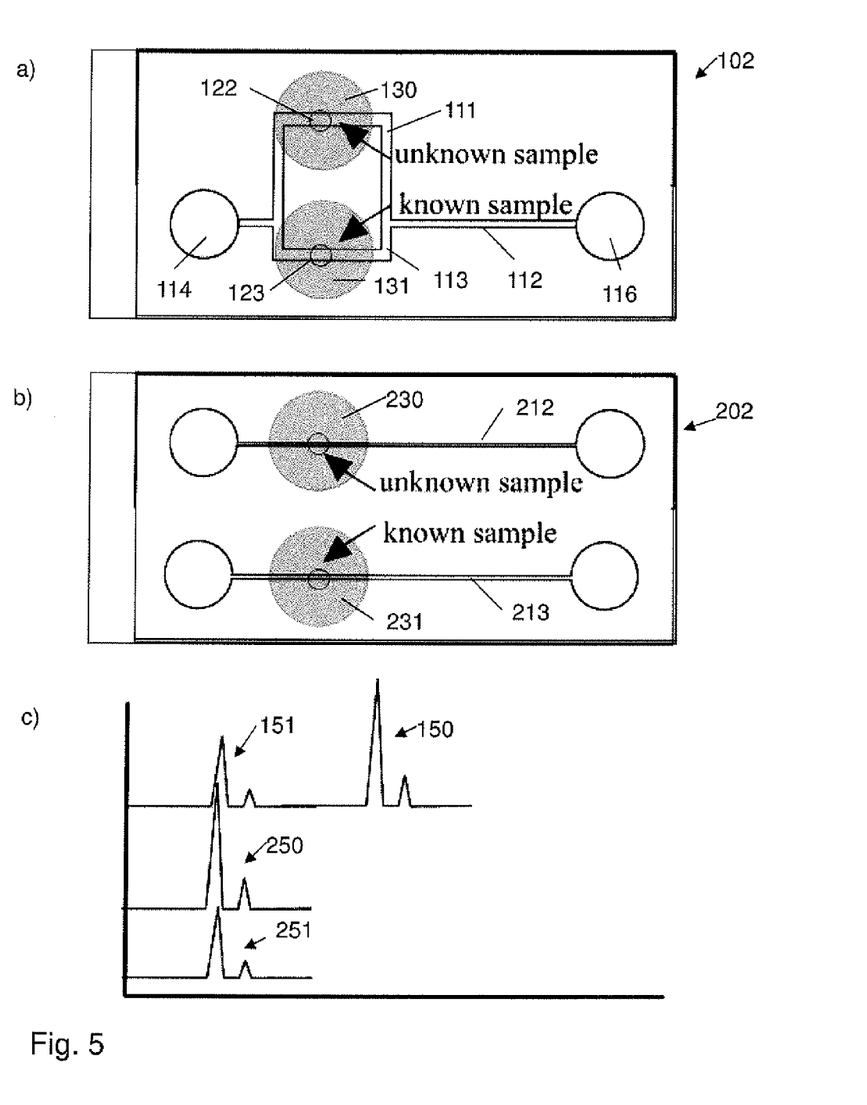
FIGS. 5a and 5b show alternative embodiments of the present invention and FIG. 5c shows examples of corresponding measurement signals.

FIGS. 5a and 5b show alternative embodiments of the present invention. These embodiments may for example be used for calibration purposes.

FIG. 5a shows an apparatus 102 according to the invention and based on the apparatus 2 described above. In this embodiment of the invention a channel 112 between a first reservoir 114 and a second reservoir 116 branches into a first channel branch 111 and a second channel branch 113. Both the first channel branch 111 and the second channel branch 113 of the channel 112 are reunited before the second reservoir 116. The first channel branch 111 is considerably longer than the second channel branch 113. Both the first channel branch 111 and the second channel branch 113 have an opening 122 and 123, respectively. The openings 122 and 123 are each covered with a membrane 130 and 131, respectively.

If two different samples 150 and 151 are each placed on separate ones of the membranes 130 and 131 and an electric field is applied along the channel 112, the ions of each of the samples will be separated and moved along the channel 112. As the first channel branch 111 is longer than the second channel branch 113, the charged species, i.e. ions, of the second sample 151 will arrive first at channel 112 while the charged species of the first sample 150 take somewhat longer. Thus both of the charged species can be measured independently one after the other with the same pair of conductivity electrodes (not shown) resulting in a signal as illustrated in the top line of FIG. 5c.

This embodiment may also be used for calibration by providing a known sample 150 to membrane 130 resulting in a corresponding first signal that can be used for calibration. The second signal from an unknown sample 151 provided to membrane 131 will arrive later in time due to the longer channel branch 111. The strength of the second signal can than be compared to the first calibration signal and the concentration of the charged components in the unknown sample can be determined as known in the art.

This embodiment might also be used with same sample provided to membrane 130 and to membrane 131 to realize higher accuracy by for instance averaging.

FIG. 5b shows an alternative embodiment 202 of the invention where two channels 212 and 213 are arranged in parallel. Each of the channels 212 and 213 are basically identical to the embodiment of FIGS. 1-4 with the advantage that two samples 250 and 251 are placed in parallel on membranes 230 and 231, respectively, so that both samples are measured in parallel. As both channels 212 and 213 are identical, the measurements can be compared. Examples are shown in the lower lines of FIG. 5c.

For calibration purposes, one sample, for example a first sample 250 can be a known sample with known ion concentrations. Thus the signal of first sample 250 can be used for calibration and compared to a signal from a second sample 251 and second channel 213 and the concentration of charged particles can be determined in a way known in the art.

It is obvious, that a plurality of channels can be arranged in parallel, for example to perform multiple measurements to accelerate throughput or to increase measurement statistics.

Figure 6:
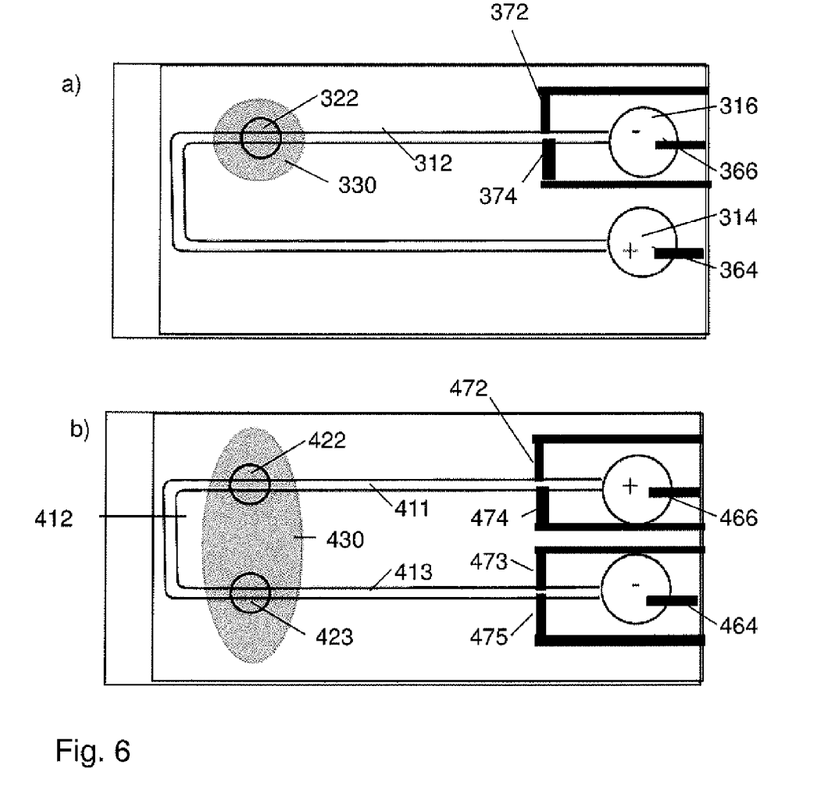
FIG. 6a shows another embodiment of the apparatus with a substantially U-shaped channel.
FIG. 6b shows a further embodiment with two opening in a single channel.

FIG. 6a shows yet another embodiment of an apparatus for the measurement of a concentration of an ion in a sample wherein a channel 312 is substantially curved and a first reservoir 314 comprising a first electrophoresis electrode 364 is place at the same side of a substrate as a second reservoir 316 comprising a second electrophoresis electrode 366. Contacts for both of the electrophoresis electrodes 364 and 366 may be guided to the side of the apparatus for easy contact to the side of the apparatus. In addition the conductivity electrodes 372 and 374 are provided in proximity to the second reservoir 366 for measuring the conductivity of charged component in the channel 312 at this position. The conductivity electrodes 372 and 374 may connected via contacts that are arranged at the same side of the apparatus or substrate as the contacts for the conductivity electrodes. In that way, only the part of the apparatus with the contacts needs to be placed into contact with a measurement device and free access to the membrane 330 placed in opening 322 can be ensured. With such an apparatus it is possible to have easy access, for example with a finger tip to the membrane 330, while the apparatus is inserted or contacted to a measurement and/or control device. The channel 312 is further straight between the opening 322 and the conductivity electrodes 372, 374 so that no bending of the channel 312 containing the sample is necessary which might influence measurement accuracy or make measurement otherwise difficult.

FIG. 6b shows a modification of the embodiment shown in FIG. 6a, further providing a second opening 423 in channel 412 that is covered by the same membrane 430 as a first opening 422. Thus a sample on membrane 430 will diffuse substantially in the same time through both of the openings 422 and 423 in the channel 412. Applying an electrical field to electrophoresis electrodes 464 and 466, will, depending on the sign of the voltage, cause for example the positively charged species or ions to move into a first channel section 411 towards a second electrophoresis electrode 466. Similarly negatively charged species are moved into a second channel section 413 towards a first electrophoresis electrode 464. The conductivity electrodes 472, 474 and 473, 475 allow for measurement of both of the positively charged species and the negatively charged species. Thus the charged species of both electrical charges can be measured in parallel.

Figure 7:
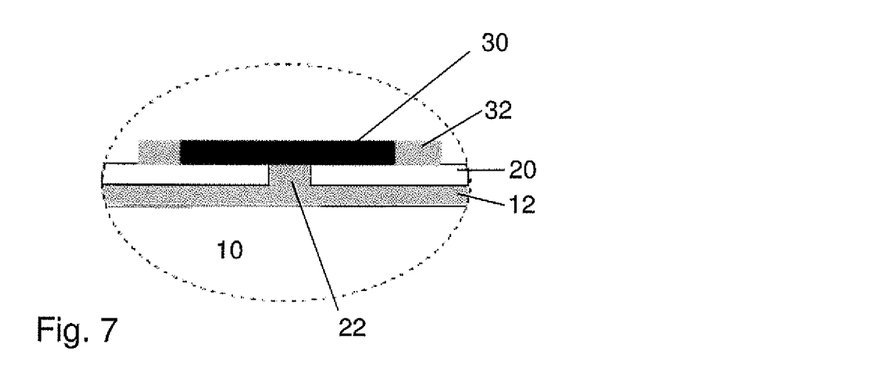
FIG. 7 shows a further embodiment of the invention with a membrane holder.

FIG. 7 shows a modification of the apparatus according to the invention shown in FIG. 2. A membrane holder 32 is mounted on top of the second layer 20. The membrane 30 is mounted, for example glued, onto or in the membrane holder 32. Thus the membrane can be assembled on the membrane holder before the membrane holder is mounted on the apparatus.

The membrane holder 32 may be made from plastics material.

In the embodiment shown the membrane holder 32 forms a "cup"-like or a ring like structure providing a receiving section for the membrane 30. The upper surface of the membrane is substantially planar with the upper rim of the "cup"-like structure of the membrane holder. The membrane holder provides thus a frame for the membrane 30 with a well defined surface area of the membrane being left for contact with the sample. In that way, the amount of sample coming in contact with the membrane can be controlled in a simple and efficient way, even when the sample is much bigger, than the membrane.

The walls of the membrane holder may also be higher than the thickness of the membrane, thereby providing a "cup"-like or ring-like structure for the sample (not shown) with the membrane at the bottom of the "cup". The cup may be used to collect the sample on the membrane.

The membrane holder 32 may enable a fast and easy exchange or replacement of the membrane 30. By exchanging the membrane 30, the apparatus can be easily adapted to different measurements, e.g. by using membranes with different pore sizes, the size of components that are filtered out or let into the channel can be adjusted to the needs of the particular measurement.

The membrane holder 32 can furthermore enable easy fixation of the membrane 30 on the first cover layer by for instance a click-and-fix method.

The membrane holder 32 can have the second cover layer 40 on top to prevent leakage, evaporation, etcetera.

Figure 8:
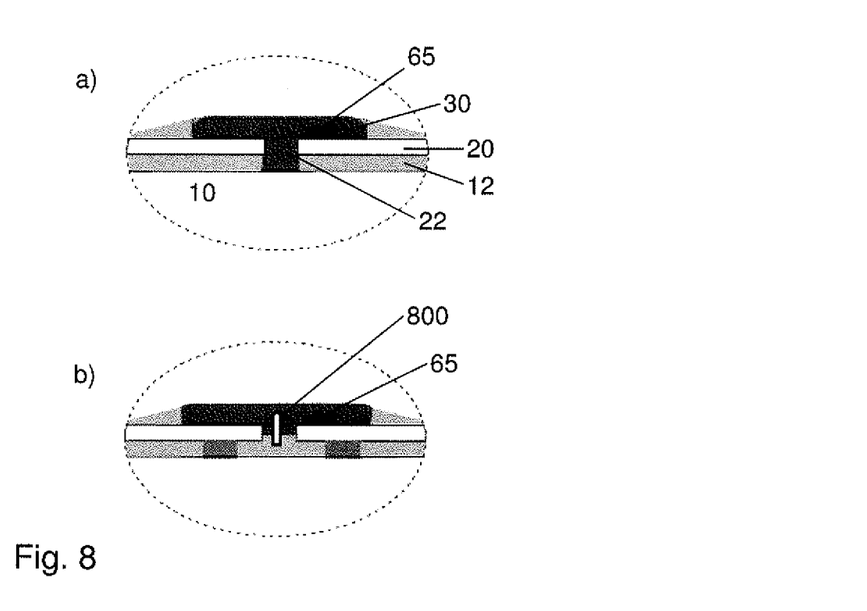
FIGS. 8a and 8b show an embodiment of the invention with an extra electrode.

FIGS. 8a and 8b show an embodiment of the present invention with an additional anti-tailing electrode 65 for preventing tailing of the sample or components inside the channel 12. The anti-tailing electrode 65 is shown in between first cover layer 20 and membrane 30. The anti-tailing electrode 65 may, however, also be arranged differently on the top side of or at the opening 22 of first cover layer 20. FIG. 8a shows the apparatus with the anti tailing electrode 65 in the same state as the apparatus shown and described with respect to FIG. 3e. The apparatus and the method described with respect to FIGS. 1 to 3 apply accordingly and the filtered sample may thus diffuse through membrane 30 and first opening 22 into channel 12 as described above.

Prior or simultaneously to applying the electrical field along the channel 12 for electrophoretically separating the portion of the filtered sample illustrated and described with respect to FIG. 3f, voltage is applied additionally to anti-tailing electrode 65. Thereby a portion of the sample component is also driven backwards through the first opening 22 towards the membrane 30 as indicated by arrow 800 in FIG. 8b. The electrical field separates the charged species in the filtered sample and move the charged species towards the reservoirs 14 and 16 at the end of the channel 12 and towards the membrane 30. Therefore, no sample component enters the channel after starting separation. This effect increases measurement accuracy.

The extra electrode 65 may also consist of a plurality of electrodes and might also be used for parameter detection prior or during measurement.

Figure 9:
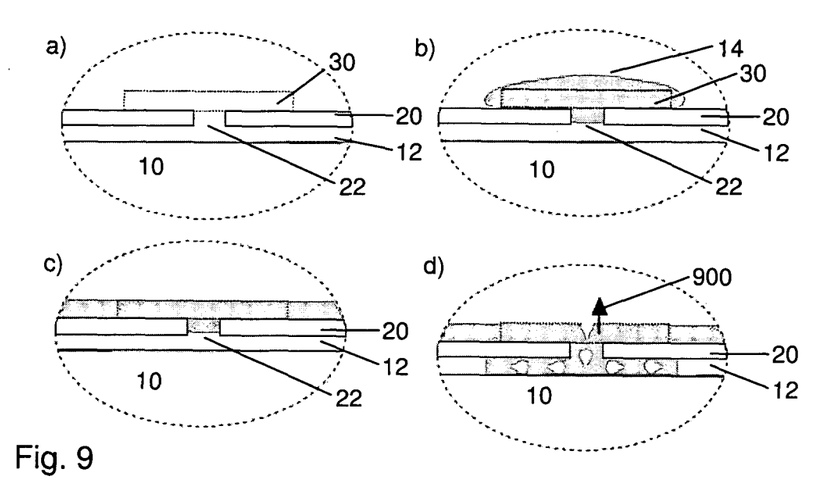
FIGS. 9a to 9d illustrate a method of the invention in which the fluid is inserted into the channel by vacuum.

FIGS. 9a to 9d show how a fluid such as the background electrolyte solution (BGE) or any other solution may be inserted into the channel 12 of the apparatus described with respect to FIGS. 1, to 3 using only one opening 22 in the channel 12. FIG. 9a illustrates the apparatus of FIG. 2 before any fluid is inserted. A droplet of fluid 14 is put on the membrane 30 as shown in FIG. 9b. The fluid 14 will then flow into the membrane 30 until it covers opening 22 of channel 12. At this point, illustrated in FIG. 9c, the fluid does not enter by itself further into the channel 12 because of the air or gas being inside the channel 12. The air of gas inside the channel 12 can only exit the channel 12 through the single opening 22, which is covered by fluid 14. FIG. 9d shows that by the application of a vacuum (indicated by arrow 900) the air or gas inside the channel 12 can be sucked out of the so that the fluid 14 enters into the channel 12.

Figure 10:
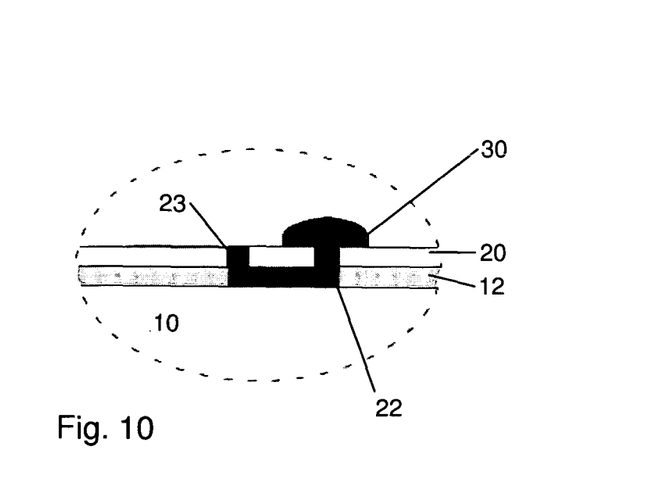
FIG. 10 shows a further embodiment of the invention in which the fluid is inserted into the channel by use of second opening in the channel.

FIG. 10 shows a further method for sampling a fluid such as blood or any other sample into the micro-channel 12. A second opening 23 may be provided at some distance of first opening 22. Both openings 22 and 23 are connected by the channel 12. Preferably, the channel 12 has no further openings that said openings 22 and 23 and is otherwise sealed. The second opening 23, however, is not covered by a membrane. Fluid inside the channel 12 may exit through the second opening 23, when the sample is applied on the first opening 22.

The second opening 23 may be covered by a polymer layer or otherwise closed, after the fluid has been filled into the channel 12, to prevent evaporation of the fluid. During sampling the second opening 23 has to be connected in any way to air and might not be covered by the sample directly.

Connections to the electrodes can be also arranged on one side of the apparatus allowing for easy attachment and connection to a measurement device. Easy access is especially important when the apparatus is in form of a disposable chip that can be inserted for one measurement into a measurement device that may be operated by the patient.

The apparatus 2 can be packaged inside a packaging with suitable interfaces to allow connection to electronics for measurement and controls, communications interfaces and display interfaces as well as for power electronics.

The openings 22 have been described as being made in the upper surface of the substrate 10. However, the openings 22 can also be realized at any other location of the apparatus 2 for instance in the side.

The apparatus 2 can be easily used by a patient to measure the concentration of ions in blood. For example, for those patients suffering from bipolar mood disorder, the patient can measure the concentration of lithium ions in the blood on a regular basis. Should the concentration go below a critical level (e.g. 0.4 mmol/L) then the patient can take extra lithium. Should the concentration go above a critical level (1.0 mmol/L), then the patient can stop or lower medication and if necessary be hospitalized.

The use of the apparatus 2 has been described with respect to the measurement of lithium ions. The apparatus 2 could also be used for the measurement of potassium and/or phosphate ions to observe the functioning of a kidney or sodium and/or potassium ions to determine dehydration.

The apparatus of the invention has applications outside of the medical field. For example, it would be desirable when using the apparatus in the environmental and other fields to be able to use the same apparatus over the course of a period of time. In this case, the apparatus might be provided with a plurality of openings 22, each of which had its own cover. The own cover would be periodically removed from different ones of the plurality of openings 22 to allow repeated measurements.

The invention has been described with respect to several embodiments. It will, however, be clear to those skilled in the

The invention claimed is:

1. A method for the measurement of a concentration of a charged species in a sample, the sample having a plurality of types of charged species and at least one insoluble component, the method comprising:
   removing a protection cover from a first layer to reveal a surface of the first layer;
   providing the sample on the surface of a first layer, wherein the first layer comprises one or more holes in the first layer providing the sample contact with a channel formed in a non-conducting substrate, wherein the channel is otherwise sealed and has at least two electrodes arranged along the channel on each side of the one or more holes
   allowing components of the sample to pass through the first layer into the channel;
   separating the components inside the channel into sections, such that each at least one of the sections substantially comprises a single type of the plurality of the types of charged species; and
   determining the species concentration in the sections.

2. The method of claim 1, further comprising measuring the conductivity of at least one of the sections.

3. The method of claim 1, wherein the concentration of a first one of the plurality of type of charged species is determined relative to a second one of the plurality of the types of charged species.

4. The method of claim 1, wherein separating the components into sections is based on capillary electrophoresis.

5. The method of claim 1, wherein the first layer is substantially impermeable to cellular material.

6. The method of claim 1, wherein the first layer consists of one opening towards the channel wherein the channel is otherwise sealed.

7. The method of claim 1, wherein the sample passes through the first layer into the channel based on a convective flow caused by a second opening in the channel.

8. The method of claim 1, further comprising determining at least one apparatus-parameter.

9. An apparatus for the measurement of a concentration of a charged species in a sample, the sample comprising a plurality of types of charged species and at least one insoluble component, the apparatus comprising:
   a non-conducting substrate;
   at least one channel formed in the non-conducting substrate and with
   one or multiple openings at the location of the sample contact area and wherein the at least one channel is otherwise closed;
   a first layer covering the at least one opening, wherein the first layer comprises one or more holes in the first layer covering the at least one channel, and wherein the at least one channel is otherwise sealed;
   a removable protection cober cobering at least pertly a surface of the first layer and the at least one opening;
   at least two electrodes arranged along the at least one channel on each side of the opening;
   and at least one sensor for measuring at least one type of charged species in the at least one channel.

10. The apparatus of claim 9, wherein the first layer is impermeable to cellular material.

11. The apparatus of claim 9, wherein the first layer comprises one opening towards the channel, wherein the channel is otherwise sealed.

12. The apparatus of claim 9, wherein the width or height of the at least one channel is 100 $\mu$m or less.

13. The apparatus of claim 9, wherein the at least one sensor comprises conductivity electrodes.

14. The apparatus of claim 9, further comprising at least one electrode arranged on the side of the at least one opening that is opposite to the channel.

15. The apparatus of claim 9, wherein the at least one channel comprises a first reservoir at a first end of the at least one channel and a second reservoir at a second end of the at least one channel, wherein the first reservoir and the second reservoir each comprise one of the electrophoresis electrodes.

16. The apparatus of claim 9, wherein the at least one channel, the electrophoresis electrodes, the at least one sensor and the first layer are integrated into the apparatus.

17. The apparatus of claim 9, wherein the at least one channel has one first opening covered by the first layer and at least one second opening, wherein the at least one channel is an otherwise sealed channel.

18. A method for the production of an apparatus comprising:
   providing a non-conducting substrate;
   providing a first layer and a protection cover;
   forming a channel into the substrate or into the first layer;
   placing said first layer on the non-conducting substrate, such that the first layer and the substrate close the channel, whereby the first layer and the substrate together comprise at least one opening providing access to the channel, wherein the first layer comprises one or more holes towards the channel, wherein the channel extends to at least one side of the at least one opening;
   placing the protection cover over the fist layer, such that the protection cover substantially seals the channel.

19. The method of claim 18, further comprising filling the channel with an electrolyte.

20. The method of claim 18, wherein filling of the channel comprises evacuating air and sucking electrolyte into the channel.

* * * * *

UNITED STATES PATENT AND TRADEMARK OFFICE
CERTIFICATE OF CORRECTION

PATENT NO.         : 8,465,637 B2
APPLICATION NO.    : 12/515635
DATED              : June 18, 2013
INVENTOR(S)        : Steven Staal et al.

Page 1 of 1

It is certified that error appears in the above-identified patent and that said Letters Patent is hereby corrected as shown below:

In the Claims

Col. 14, Claim 9, line 3, "a removable protection cober cobering at least pertly a"
should read -- a removable protection cover covering at least partly a --.

Signed and Sealed this
First Day of October, 2013

Teresa Stanek Rea
*Deputy Director of the United States Patent and Trademark Office*